US009615785B2

(12) United States Patent
Röcker et al.

(10) Patent No.: US 9,615,785 B2
(45) Date of Patent: Apr. 11, 2017

(54) METHOD AND APPARATUS TO DETERMINE THE OVERALL FITNESS OF A TEST SUBJECT

(75) Inventors: Kai Röcker, Freiburg (DE); Albert Gollhofer, Stegen (DE)

(73) Assignee: adidas AG, Herzogenaurach (DE)

( * ) Notice: Subject to any disclaimer, the term of this patent is extended or adjusted under 35 U.S.C. 154(b) by 92 days.

(21) Appl. No.: 13/262,289

(22) PCT Filed: Mar. 31, 2010

(86) PCT No.: PCT/DE2010/000371
§ 371 (c)(1),
(2), (4) Date: Oct. 20, 2011

(87) PCT Pub. No.: WO2010/112010
PCT Pub. Date: Oct. 7, 2010

(65) Prior Publication Data
US 2012/0029370 A1 Feb. 2, 2012

(30) Foreign Application Priority Data
Apr. 1, 2009 (DE) .................. 10 2009 015 273

(51) Int. Cl.
*A61B 5/02* (2006.01)
*A61B 5/22* (2006.01)
(Continued)

(52) U.S. Cl.
CPC .............. *A61B 5/222* (2013.01); *A61B 5/024* (2013.01); *A63B 24/0062* (2013.01);
(Continued)

(58) Field of Classification Search
USPC ................................................ 600/508–528
See application file for complete search history.

(56) References Cited

U.S. PATENT DOCUMENTS 3,742,937 A 7/1973 Manuel et al.
3,802,698 A 4/1974 Burian et al.
(Continued)

FOREIGN PATENT DOCUMENTS

AT 407824 11/2000
CN 1448876 A 10/2003
(Continued)

OTHER PUBLICATIONS

German Patent Office, Counterpart Patent Application DE 10 2009 015 273.3, Search Report—issued Dec. 8, 2009.
(Continued)

*Primary Examiner* — Christopher D Koharski
*Assistant Examiner* — Elizabeth K So
(74) *Attorney, Agent, or Firm* — Sterne, Kessler, Goldstein & Fox P.L.L.C.

(57) ABSTRACT

A procedure and apparatus to determine the overall fitness of a test subject. For this purpose the qualitative and temporal progression of the heart rate under constant physical stress of the subject is prescribed with at least one parameter dependent on the subject. The heart rate of the subject is measured under constant physical stress during a period of time. The parameter(s) are determined from the measured values, and the maximum heart rate and/or the initial heart rate and/or the increase characteristic of the heart rate are determined from the function and the measured values by numerical procedures. The apparatus can measure the heart rate of the subject, record a temporal progression of the heart rate under physical stress, and determines numerically from the temporal progression of the heart rate, the maximum heart rate and/or the initial heart rate without physical stress and/or the increase characteristic of the heart rate.

17 Claims, 3 Drawing Sheets

Figure 1:
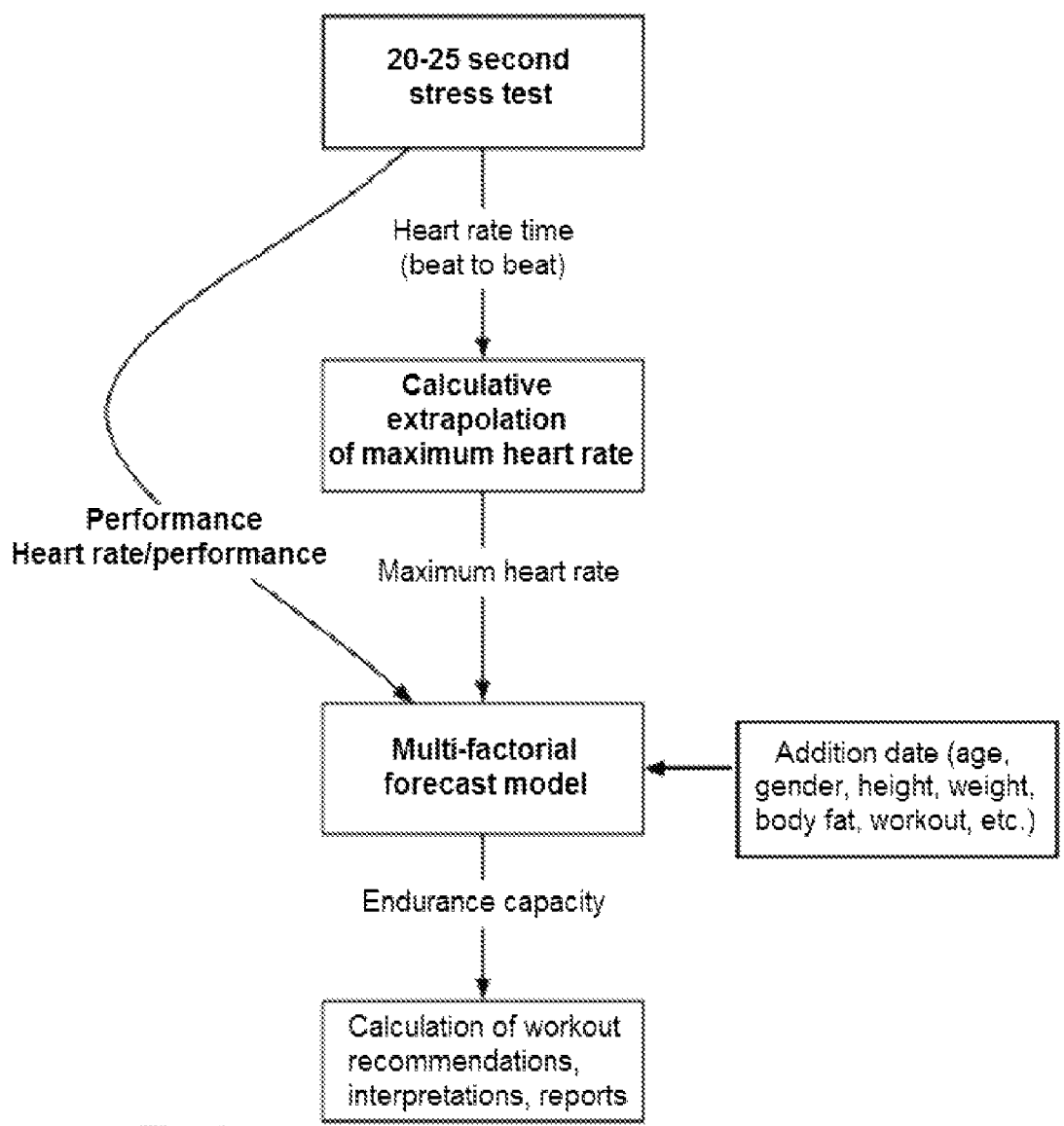

(51) Int. Cl.
*A61B 5/024* (2006.01)
*A63B 24/00* (2006.01)
*A63B 22/02* (2006.01)

(52) U.S. Cl.
CPC .......... *A63B 24/0075* (2013.01); *A63B 22/02* (2013.01); *A63B 2024/0065* (2013.01); *A63B 2220/30* (2013.01); *A63B 2220/51* (2013.01); *A63B 2220/62* (2013.01); *A63B 2230/06* (2013.01); *A63B 2230/20* (2013.01)

(56) References Cited

U.S. PATENT DOCUMENTS

| | | |
|---|---|---|
| 3,838,684 A | 10/1974 | Manuel et al. |
| 3,978,849 A | 9/1976 | Geneen |
| 4,027,663 A | 6/1977 | Fischler et al. |
| 4,038,976 A | 8/1977 | Hardy et al. |
| 4,120,294 A | 10/1978 | Wolfe |
| 4,120,296 A | 10/1978 | Prinz |
| 4,221,223 A | 9/1980 | Linden |
| 4,248,244 A | 2/1981 | Charnitski et al. |
| 4,252,128 A | 2/1981 | Kane |
| 4,364,556 A | 12/1982 | Otte |
| 4,436,096 A | 3/1984 | Dyck et al. |
| 4,647,217 A | 3/1987 | Havel |
| 4,653,498 A | 3/1987 | New, Jr. et al. |
| 4,776,323 A | 10/1988 | Spector |
| 4,788,983 A | 12/1988 | Brink et al. |
| 4,938,228 A | 7/1990 | Righter et al. |
| 5,158,093 A * | 10/1992 | Shvartz et al. ............... 600/520 |
| 5,314,389 A | 5/1994 | Dotan |
| 5,686,938 A | 11/1997 | Batkhan |
| 5,697,791 A | 12/1997 | Nashner et al. |
| 5,735,799 A | 4/1998 | Baba et al. |
| 5,769,755 A | 6/1998 | Henry et al. |
| 5,857,939 A | 1/1999 | Kaufman |
| 5,891,042 A | 4/1999 | Sham et al. |
| 5,976,083 A | 11/1999 | Richardson et al. |
| 6,002,982 A | 12/1999 | Fry |
| 6,010,430 A | 1/2000 | Mankovtiz |
| 6,013,007 A | 1/2000 | Root et al. |
| 6,050,924 A | 4/2000 | Shea |
| 6,080,110 A | 6/2000 | Thorgersen |
| 6,080,111 A | 6/2000 | Pao-Lang |
| 6,104,947 A | 8/2000 | Heikkila et al. |
| 6,133,722 A | 10/2000 | Havel |
| 6,135,951 A | 10/2000 | Richardson et al. |
| 6,148,262 A | 11/2000 | Fry |
| 6,163,718 A | 12/2000 | Fabrizio |
| 6,230,047 B1 | 5/2001 | McHugh |
| 6,244,988 B1 | 6/2001 | Delman |
| 6,251,048 B1 | 6/2001 | Kaufman |
| 6,345,197 B1 | 2/2002 | Fabrizio |
| 6,394,960 B1 | 5/2002 | Shinogi et al. |
| 6,463,385 B1 | 10/2002 | Fry |
| 6,572,636 B1 | 6/2003 | Hagen et al. |
| 6,582,342 B2 | 6/2003 | Kaufman |
| 6,585,622 B1 | 7/2003 | Shum et al. |
| 6,607,493 B2 | 8/2003 | Song |
| 6,716,139 B1 | 4/2004 | Hosseinzadeh-Dolkhani et al. |
| 6,734,837 B1 | 5/2004 | Havel |
| 6,736,759 B1 | 5/2004 | Stubbs et al. |
| 6,745,069 B2 | 6/2004 | Nissila et al. |
| 6,749,432 B2 | 6/2004 | French et al. |
| 6,753,882 B2 | 6/2004 | Nakazawa et al. |
| 6,758,816 B1 | 7/2004 | Tsubata et al. |
| 6,798,378 B1 | 9/2004 | Walters |
| 6,823,036 B1 | 11/2004 | Chen |
| 6,832,109 B2 | 12/2004 | Nissila |
| 6,837,827 B1 | 1/2005 | Lee et al. |
| 6,853,955 B1 | 2/2005 | Burrell et al. |
| 6,882,955 B1 | 4/2005 | Ohlenbusch et al. |
| 7,057,551 B1 | 6/2006 | Vogt |
| 7,062,225 B2 | 6/2006 | White |
| 7,076,291 B2 | 7/2006 | Pulkkinen et al. |
| 7,081,809 B1 | 7/2006 | Mix et al. |
| 7,085,678 B1 | 8/2006 | Burrell et al. |
| 7,097,588 B2 | 8/2006 | Watterson et al. |
| 7,192,387 B2 | 3/2007 | Mendel |
| 7,192,402 B2 | 3/2007 | Amano et al. |
| 7,220,220 B2 | 5/2007 | Stubbs et al. |
| 7,229,385 B2 | 6/2007 | Freeman et al. |
| 7,251,454 B2 | 7/2007 | White |
| 7,254,516 B2 | 8/2007 | Case, Jr. et al. |
| 7,264,554 B2 | 9/2007 | Bentley |
| 7,292,867 B2 | 11/2007 | Werner et al. |
| 7,383,081 B2 | 6/2008 | Butt et al. |
| 7,398,151 B1 | 7/2008 | Burrell et al. |
| 7,480,512 B2 | 1/2009 | Graham et al. |
| 7,518,054 B2 | 4/2009 | McKinney et al. |
| 7,519,327 B2 | 4/2009 | White |
| 7,603,255 B2 | 10/2009 | Case, Jr. et al. |
| 7,648,463 B1 | 1/2010 | Elhag et al. |
| 7,670,263 B2 | 3/2010 | Ellis et al. |
| 7,689,283 B1 | 3/2010 | Schecter |
| 7,758,469 B2 | 7/2010 | Dyer et al. |
| 7,766,794 B2 | 8/2010 | Oliver et al. |
| 7,771,320 B2 | 8/2010 | Riley et al. |
| 7,909,737 B2 | 3/2011 | Ellis et al. |
| 7,927,253 B2 | 4/2011 | Vincent et al. |
| 8,001,472 B2 | 8/2011 | Gilley et al. |
| 8,033,959 B2 | 10/2011 | Oleson et al. |
| 8,052,580 B2 | 11/2011 | Saalasti et al. |
| 8,068,858 B2 | 11/2011 | Werner et al. |
| 8,103,517 B2 | 1/2012 | Hinnebusch |
| 8,105,208 B2 | 1/2012 | Oleson et al. |
| 8,121,785 B2 | 2/2012 | Swisher et al. |
| 8,360,936 B2 | 1/2013 | DiBenedetto et al. |
| 8,529,407 B2 | 9/2013 | Nurmela et al. |
| 2001/0003542 A1 | 6/2001 | Kita |
| 2002/0055419 A1 | 5/2002 | Hinnebusch |
| 2002/0068873 A1 | 6/2002 | Nissila |
| 2002/0156386 A1 * | 10/2002 | Dardik ................. A61B 5/0002 600/520 |
| 2002/0198463 A1 | 12/2002 | Dardik et al. |
| 2003/0028116 A1 | 2/2003 | Bimbaum |
| 2003/0069108 A1 | 4/2003 | Kaiserman et al. |
| 2003/0171189 A1 | 9/2003 | Kaufman |
| 2003/0224337 A1 | 12/2003 | Shum et al. |
| 2004/0046692 A1 | 3/2004 | Robson et al. |
| 2004/0102931 A1 | 5/2004 | Ellis et al. |
| 2004/0116784 A1 | 6/2004 | Gavish |
| 2004/0171956 A1 | 9/2004 | Babashan |
| 2004/0199056 A1 | 10/2004 | Husemann et al. |
| 2005/0049113 A1 | 3/2005 | Yuch et al. |
| 2005/0124463 A1 | 6/2005 | Yeo et al. |
| 2005/0181347 A1 | 8/2005 | Barnes et al. |
| 2005/0195094 A1 | 9/2005 | White |
| 2005/0197063 A1 | 9/2005 | White |
| 2005/0256416 A1 | 11/2005 | Chen |
| 2005/0266961 A1 | 12/2005 | Shum et al. |
| 2006/0136173 A1 | 6/2006 | Case, Jr. et al. |
| 2006/0169125 A1 | 8/2006 | Ashkenazi et al. |
| 2006/0189360 A1 | 8/2006 | White |
| 2006/0253210 A1 | 11/2006 | Rosenberg |
| 2007/0006489 A1 | 1/2007 | Case, Jr. et al. |
| 2007/0011919 A1 | 1/2007 | Case, Jr. |
| 2007/0021269 A1 | 1/2007 | Shum |
| 2007/0033069 A1 | 2/2007 | Rao et al. |
| 2007/0159926 A1 | 7/2007 | Prstojevich et al. |
| 2007/0232455 A1 | 10/2007 | Hanoun |
| 2007/0260421 A1 | 11/2007 | Berner, Jr. et al. |
| 2007/0287596 A1 | 12/2007 | Case et al. |
| 2008/0002528 A1 | 1/2008 | Andren et al. |
| 2008/0004510 A1 | 1/2008 | Tanzawa et al. |
| 2008/0009275 A1 | 1/2008 | Werner et al. |
| 2008/0033311 A1 | 2/2008 | Sledge |
| 2008/0051993 A1 | 2/2008 | Graham et al. |
| 2008/0058971 A1 | 3/2008 | Graham et al. |
| 2008/0059064 A1 | 3/2008 | Werner et al. |
| 2008/0065319 A1 | 3/2008 | Graham et al. |
| 2008/0096726 A1 | 4/2008 | Riley et al. |
| 2008/0101161 A1 | 5/2008 | Imai et al. |
| 2008/0103689 A1 | 5/2008 | Graham et al. |

(56) References Cited

U.S. PATENT DOCUMENTS

| | | |
|---|---|---|
| 2008/0171636 A1 | 7/2008 | Usui et al. |
| 2008/0200310 A1 | 8/2008 | Tagliabue |
| 2008/0319661 A1 | 12/2008 | Werner et al. |
| 2009/0047645 A1 | 2/2009 | Dibenedetto et al. |
| 2009/0048044 A1 | 2/2009 | Oleson et al. |
| 2009/0048070 A1 | 2/2009 | Vincent et al. |
| 2009/0233769 A1 | 9/2009 | Pryor |
| 2009/0233770 A1 | 9/2009 | Vincent et al. |
| 2009/0233771 A1 | 9/2009 | Quatrochi et al. |
| 2010/0056341 A1 | 3/2010 | Ellis et al. |
| 2010/0075806 A1 | 3/2010 | Montgomery |
| 2010/0292050 A1 | 11/2010 | DiBenedetto et al. |
| 2010/0292599 A1 | 11/2010 | Oleson et al. |
| 2010/0292600 A1 | 11/2010 | Dibenedetto et al. |
| 2012/0244995 A1 | 9/2012 | Dibenedetto et al. |
| 2014/0249661 A1 | 9/2014 | Dibenedetto et al. |

FOREIGN PATENT DOCUMENTS

| | | |
|---|---|---|
| DE | 3920526 | 1/1991 |
| DE | 601 29 972 | 5/2008 |
| DE | 10 2007 025 664 | 1/2009 |
| EP | 1195135 B1 | 4/2002 |
| EP | 2025369 A2 | 2/2009 |
| GB | 2187554 | 9/1987 |
| JP | H11-118953 | 4/1999 |
| JP | 2001-235560 | 8/2001 |
| JP | 2002-369709 A | 12/2002 |
| JP | 3094882 U | 4/2003 |
| JP | 2009-050699 A | 3/2009 |
| WO | 00/40151 | 7/2000 |
| WO | WO-02/067449 A2 | 8/2002 |
| WO | WO-2006/065679 A2 | 6/2006 |
| WO | WO-2008/101168 A2 | 8/2008 |
| WO | WO-2009/033034 A1 | 3/2009 |

OTHER PUBLICATIONS

Agnes Wittmann-Regis, International Preliminary Report on Patentability, Parent PCT Application: PCT/DE2010/000371, issued Nov. 1, 2011, WIPO—Geneva, Switzerland.

* cited by examiner

METHOD AND APPARATUS TO DETERMINE THE OVERALL FITNESS OF A TEST SUBJECT

STATE OF THE ART

The invention relates to a procedure and an apparatus to determine the overall fitness of a test subject.

The overall fitness of a human test subject is determined by its endurance. Endurance capacity depends on various physiological factors. These include for example, age, gender, height, weight, body fat and the extent of a test subject's workout. Endurance capacity can be determined, for example, by the maximum heart rate, initial heart rate and/or the increase pattern of the heart rate during physical activity. In connection with performance diagnostics, the most precise determination possible of endurance is of great interest. For instance, endurance is an important forecasting factor for the risk of developing cardiovascular disease. Moreover endurance is a good measure for the ability to cope with everyday physical demands. In addition the success of athletic or preventive training can be optimized or objectified by taking endurance performance into account. Precise measurement of endurance in performance diagnostics thus enables, for example, the issuing of workout recommendations for leisure sports, workout control in endurance sports, workout regulation in rehabilitation, objective performance forecasting for competitive sports, the determination or evaluation of a functional impairment in the case of severe, chronic medical disorders, such as heart failure, pre-operative evaluation for specific diseases, for example on a question of a heart transplant or partial lung resection, the evaluation of occupational health and preventative sports.

Procedures for determining endurance capacity (or performance) are known from performance diagnostics in which the test subject undergoes a stress test which matches in form and duration the stress for which a statement is to be made. For example a test of about 30 minutes occurs with increasing load intensity on a treadmill to measure performance in long-distance running. In such a test, in addition to physical performance, heart rate and lactate concentration in the blood are determined as well. Evidence on performance in long-distance running can be obtained with great precision by the temporal progression of these metrics. Appropriate stress tests are known for other areas. For this purpose, for example, ergometers are used for bicycles, rowing machines, canoes, hand bikes and hand cranks. The so-called anaerobic threshold is often used as a benchmark for endurance. This value can be determined from the results of a performance diagnostic by using various methods.

The well-known procedures to determine the overall fitness of a test subject have the disadvantage of being very costly in time and equipment and are associated with very high physical demands on the person being tested. These high physical demands as well as high expenses for payments and staff to carry out the known methods have thus far prevented a wide application, for example, in fitness rooms and gymnasiums as well as with athletic companies. There are also methods known in which endurance capacity can be determined without physical strain, however these lead to inaccurate results.

The task of the invention is to make a procedure and an apparatus available to determine the overall fitness of a test subject, which lead to an exact and reproducible result without exposing the subject to high physical strain over a long period, and without relying on a high cost of time and equipment.

THE INVENTION AND ITS ADVANTAGES

The task is resolved by a procedure and an apparatus as described herein. The procedure according to the invention is characterized by the qualitative temporal progression of the heart rate during constant physical strain as a mathematical function with at least one parameter entered relative to the test subject. This takes advantage of the fact that the heart rate exhibits a known typical progression characteristic at the onset of sudden physical stress. The temporal progression of the heart rate is characterized by a first segment with an initially slow increase at the start of physical stress, followed by a second segment with rapid increase as the physical stress is maintained, and then a third segment with a decreasing trend of the heart rate. The second segment typically begins after 3 to 5 seconds of the physical workout. In the third segment the heart rate approaches a stable value, whereby this value no longer changes within a given measurement precision during prolonged constant physical stress. It is designated as the maximum heart rate of this form of strain. This value is typically reached after 2 to 3 minutes of physical exercise. Due to the initially slow increase, followed by a segment with a more rapid increase and an approach to the maximum value, the course qualitatively equals the curve of a hyperbola. The time intervals of the first, second and third segments, as well as the maximum and minimum values of the heart rate, are different from one subject to another, and also depend on the intensity and the duration of the strain. The qualitative temporal progression of the heart rate however is the same for all test subjects and all types of physical strain. The parameters of this function are determined by measuring the heart rate of a subject under constant physical stress. Typically a constant physical stress lasting from 5 to 50 seconds is enough for this. For most subjects a physical stress lasting from 20 to 30 seconds is sufficient to determine the parameters of the mathematical function with high accuracy. If the parameters of the function are ascertained, the maximum heart rate can be determined by numerical procedures, for example, extrapolation. Non-linear procedures to optimize parameters, for example, are appropriate to use in determining parameters from measured values of the heart rate. These include, for instance, a so-called curve-fitting by using the Marquard-Levenberg algorithm.

The initial heart rate corresponds to the heart rate of a test subject at rest without physical stress. Often the subject already has an elevated heart rate compared to the initial heart rate at the beginning of the measurement of his heart rate, as he has already moved previously, even only a little, or is excited. The output heart rate can be determined from the function provided with ascertained parameters by means of numerical procedures, for example, extrapolation.

Furthermore the increase characteristics of the heart rate over time can be determined from the function provided with parameters. This includes, for example, the maximum slope of the function. Precisely as the maximum heart rate and the initial heart rate do, it gives an indication of the overall fitness of a subject, especially of his endurance capacity.

The maximum heart rate, the initial heart rate and the increase characteristic can be determined alternatively or cumulatively. Any pair of the quantities can also be determined.

To determine the overall fitness of a test subject it is sufficient for the subject to undergo a constant physical workout within a brief period of less than 50 seconds and during this time the heart rate of the subject is continuously measured. For this purpose, the subject performs a physical movement with cardiopulmonary strain. The subject must neither begin with the physical workout at his initial heart rate nor undergo it until reaching his maximum heart rate. With reference to the three segments of the increase of heart rate in a physical workout mentioned earlier, the measured values of the heart rate are preferably determined in the second segment. The values of the heart rate necessary to determine the overall fitness are measured before the subject begins to perspire. The procedure used by the invention can thus be applied in sports shops and informational events.

The determination of the maximum heart rate and/or the initial heart rate and/or increase characteristic of the heart rate results from the measured values of the heart rate by means of mathematical formulas. A computer can be used for this purpose. The procedure according to the invention is distinguished by low cost in terms of hardware and time. Moreover the test subject must undergo merely a brief physical workout. Toggle-running, squatting jumps, bicycling on an ergometer, running on a treadmill or using a stair-climber or some other ergometer, for example, are suitable for this. Due to the brief duration of typically under 60 seconds, the workout is so short that the subject is not physically exhausted from it.

Since the determination of the maximum heart rate comes about by using a physical stress test of a subject, the procedure delivers accurate values applicable to the subject.

Endurance capacity and other relevant quantities, for example, a recommendation for a body workout of the subject, can be calculated based on the maximum heart rate and/or the initial heart rate and/or the increase characteristic. A multivariant model calculation is suitable for this, for example. By means of mathematical-statistical methods, determining factors can be filtered out from a set of possibilities which indicate a significant predicative potential for a desired target quantity. An example of this type of procedure is Stepwise Multiple Regression. The procedure according to the invention enables, for example, the determination of performance at the anaerobic threshold with great accuracy. Other physiological factors of a test subject can be considered for targeting exact and reproducible values for endurance capacity, for example, age, gender, body size, weight, body fat, or abdominal or femoral girth. By considering this anamnetical information, the accuracy of endurance capacity derived from the measured values can be increased.

Along with the determination of endurance capacity, additional information for a workout recommendation for a test subject can be ascertained with the procedure according to the invention. For example it can be determined how high the heart rate should climb for an optimal endurance workout. Moreover a recommendation can be made for performance during a body workout. In a running workout, for example, the speed is entered at which the test subject should be moving forward. Furthermore the effect of an endurance workout can be determined from the relationship between performance and maximum heart rate. For this, the performance during physical stress must be determined in addition to the heart rate.

In an advantageous embodiment of the invention, an ongoing calculative plausibility test can occur to improve the result. On the basis of this plausibility test the physical stress for example can be terminated at an earlier point in time or even prolonged to a certain duration. This is the case, for example, when the determination of the parameters of the mathematical function is concluded after a short time, or when the measurement must be repeated for reasons of quality. The test subject can be informed about this with an optical indicator.

In another advantageous embodiment of the procedure according to the invention, the performance of the test subject is additionally determined during physical stress. With physical stress in the form of a toggle-run or squatting jumps, the performance can be determined, for example, by means of a measuring plate for measuring ground reaction forces. Performance is calculated from the frequency of paces and from the force exerted onto the measuring plate. If the test subject undergoes physical stress on an ergometer, the performance can be determined by means of detectors integrated into the ergometer for repetition rates and/or force. By noting maximum heart rate in relationship to associated performance, endurance capacity can be determined with better quality and accuracy. Moreover the establishment of other relevant quantities is possible. Among these, for example, is the heart rate of the test subject for an optimal endurance workout.

In another advantageous embodiment of the procedure according to the invention, the performance is monitored during the time period and held constant within pre-determined limits. Physical stress with constant performance during the measurement of the heart rate has the advantage that the maximum heart rate can be determined with great accuracy.

In another advantageous embodiment of the procedure according to the invention, the test subject is informed about adherence to and/or deviation from constant performance. During the physical stress he is thereby motivated and maintained to move with constant performance.

In another advantageous embodiment of the procedure according to the invention, endurance capacity is determined from the maximum heart rate and/or the output heart rate and/or the increase characteristic of the heart rate. Thus the performance of the test subject can be considered during physical stress. A multivariant model calculation and/or a multifactorial forecast model is suitable to determine endurance capacity.

In another advantageous embodiment of the procedure according to the invention, the parameters of the function are determined at every heartbeat detected in the test subject. This enables an especially rapid calculation of the parameters.

In another advantageous embodiment of the procedure according to the invention, the measurement of the heart rate is ended, when the parameters from at least two successive heartbeats differentiate by less than a pre-determined value. Furthermore the measurement of the heart rate can be continued under physical stress as long as the slope of the associated heart rate-time function continues to climb. It can, for example, be ended as soon as the slope falls.

In another advantageous embodiment of the procedure according to the invention, the qualitative temporal progression of the heart rate is determined as a mathematical function of the temporal progression of multiple test subjects under physical stress.

In another advantageous embodiment of the procedure according to the invention, the predominant portion of muscular mass of the test subject is put under dynamic and constant strain during physical stress. For this purpose the subject is subjected to physical stress in which the muscles of the arms, legs and upper torso are exerted. For example, in toggle-running additional weights can be carried in the hands and moved. In physical stress of the entire muscular mass the need for metabolizing oxygen is high, which results in a very accurate result for the maximum heart rate.

The apparatus according to the invention with the features of claim 12 are distinguished by being equipped with an installation to measure the heart rate of the test subject with a storage device to record a mathematical function for the temporal progression of the heart rate under physical stress and with a calculating device to calculate the parameters of the mathematical function from the measured values of the heart rate and to numerically determine the maximum heart rate and/or the initial heart rate without physical stress and/or the increase characteristic of the heart rate from the function provided with the calculated parameters. A computer, for example, is suitable for this.

In another advantageous embodiment of the apparatus according to the invention, this is equipped with a device to execute a physical movement with cardiopulmonary strain of a test subject. This can involve, for example, a bicycle ergometer, a rowing machine ergometer, a canoe ergometer, a handbike ergometer, a hand crank ergometer or a treadmill.

In another advantageous embodiment of the apparatus according to the invention, this is equipped with a device to determine performance generated by movement.

In another advantageous embodiment of the apparatus according to the invention, this is equipped with a plate to measure ground reaction forces.

Other advantages and advantageous embodiments of the invention can be found in the following description, the drawings and the claims.

FIGURE

Figure 2:
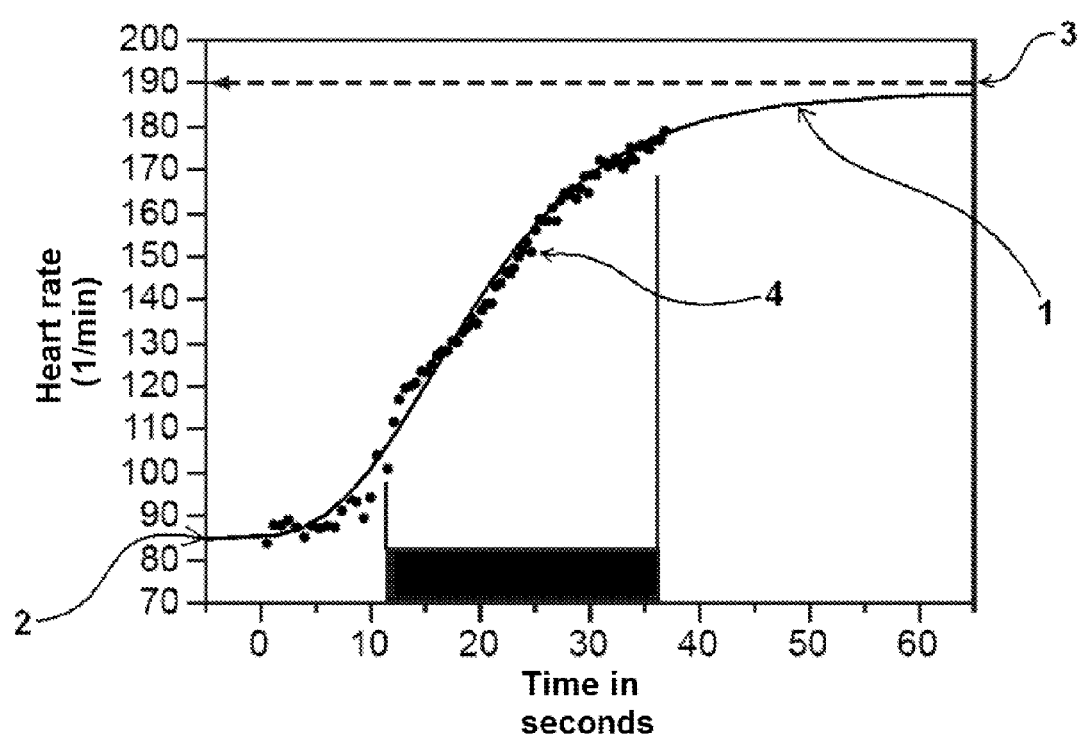
Figure 3:
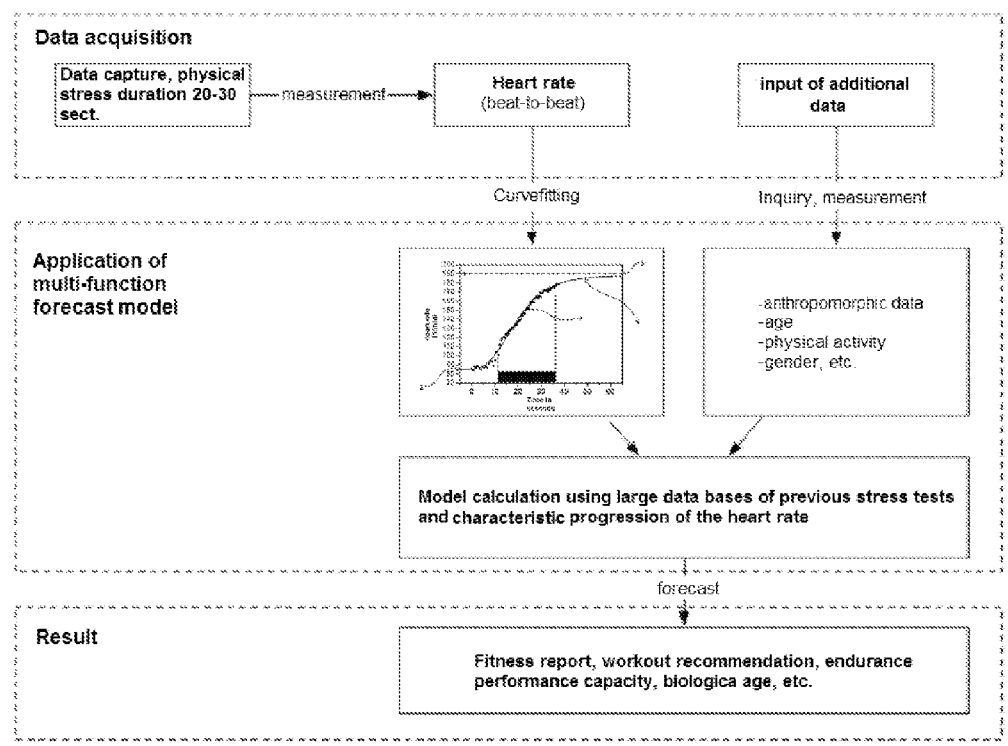

The procedural steps of the invention are schematically represented in the Figures, which show the following:

FIG. 1 Flow diagram of the procedure to determine endurance capacity,

FIG. 2 Typical temporal progression of heart rate under physical stress,

FIG. 3 Schematic illustrations of data capturing and the determination of the overall fitness of a test subject.

In the procedure schematically depicted in FIG. 1 a test subject undergoes a stress test for a duration of 20 to 25 seconds. For this purpose the subject carries out a movement with or without an exercise device with cardiopulmonary strain. During the stress test the heart rate is constantly measured so that every heartbeat is noted. By calculative extrapolation the measured values and mathematical function represented in FIG. 2 are used to determine the maximum heart rate of the subject. Parallel to this the performance of the subject is ascertained during the stress test. The relationship between heart rate and performance can also be determined. Those flow together with the maximum heart rate into a multifunctional forecast model. Moreover other physiological factors of the subject are entered, such as age, gender, body size, weight, body fat and extent of the subject's workout. Endurance capacity is determined from all quantities entered. This is used for calculating workout recommendations, interpretations and reports on the subject.

FIG. 2 shows as an example the mathematical function of a test subject's heart rate over time during physical stress. The associated curve 1 begins at initial heart rate 2, which the test subject exhibits while at rest without physical stress and without mental tension. In an initial segment up to 5 seconds the heart rate climbs only slightly. In a second segment from 5 seconds to 35 seconds the heart rate increases rapidly. In a third segment after 35 seconds the slope falls. The heart rate approaches the maximum heart rate 3. The subject begins at time-point 0 seconds with a stress workout. From 12 seconds to 35 seconds the heart rate is measured. After this both the measurement and the stress workout can be ended. The measured values of the heart rate are represented by points 4. The curve is determined from measured values by means of curve fitting. Moreover the parameters of the associated mathematical function are determined.

In FIG. 3 the capturing of data and the determination of the overall fitness of a test subject are schematically represented. The heart rate under physical stress is measured as data from 20 to 30 seconds and physical data of the subject is retrieved. From the measured data of the heart rate and the qualitative pre-determined temporal progression of the heart rate, the associated mathematical function is ascertained by means of curve fitting. The image represented corresponds to FIG. 2. From the function of the data retrieved from the subject and by means of model calculation, endurance capacity, a report concerning fitness, workout recommendation and biological age of the test subject are determined. Here one is dealing with approximate values which have a high level of accuracy.

All features of the invention can be essential to the invention both individually and in any combination with each other.

The invention claimed is:

1. A method to determine the overall fitness of a test subject comprising the following procedural steps:
    entering of a qualitative temporal progression of a heart rate under constant physical stress of a subject as a mathematical function with at least one parameter dependent on the subject,
    measuring of the heart rate of the test subject under continuous physical strain during a period of time,
    determining the parameter(s) of the mathematical function from the measured values,
    determining by a numerical process an increase characteristic of the heart rate from the maximum slope of the function and the measured values;
    wherein the test subject undergoes a constant physical workout within a brief period of less than 50 seconds and during the brief period the heart rate of the test subject is continuously measured.

2. The method according to claim 1, further comprising determining additionally a performance of the subject during physical stress.

3. The method according to claim 2, further comprising monitoring performance during the time period and maintaining it within pre-determined limits.

4. The method according to claim 3, further comprising informing the subject about deviation from constant performance.

5. The method according to claim 1, further comprising determining endurance capacity from the initial heart rate and/or the increase characteristic of the heart rate.

6. The method according to claim 5, further comprising entering physical features the subject and considering them in determining endurance capacity.

7. The method according to claim 1, further comprising determining a workout recommendation for the subject from the increase characteristic of the heart rate.

8. The method according to claim 1, further comprising calculating the parameters of the mathematical function at each heartbeat determined from the subject.

9. The method according to claim 8, further comprising terminating the measurement of the heart rate when the parameters determined from at least two successive heartbeats differ by less than a pre-determined value.

10. The method according to claim 1, further comprising determining the qualitative temporal progression of the heart rate as a mathematical function the temporal progression of the heart rate of multiple subjects under physical stress.

11. The method according to claim 1, wherein during physical stress the predominant portion of the muscular mass of the subject is under stress constantly and dynamically.

12. The method according to claim 1, wherein the maximum heart rate is determined from the increase characteristic of the heart rate determined from the function and the measured values.

13. The method according to claim 1, wherein the initial heart rate is determined from the increase characteristic of the heart rate determined from the function and the measured values.

14. An apparatus to determine the overall fitness of a subject, comprising a device to measure the heart rate of the subject, a storage device to record a mathematical function for the temporal progression the heart rate under physical stress, and a calculating device configured to calculate parameters of the mathematical function from the measured values of the heart rate and to determine numerically the increase characteristic of the heart rate from the maximum slope of the function provided with the calculated parameters, wherein the device to measure the heart rate of the subject is configured to continuously measure the rate of the subject during a brief period of less than 50 seconds within which the subject undergoes a constant physical workout.

15. The apparatus according to claim 14, further comprising a device to carry out physical movement with cardiopulmonary strain on a subject.

16. The apparatus according to claim 15, further comprising a device to determine performance generated during movement.

17. The apparatus according to claim 14, further comprising a plate to measure ground reaction forces.

* * * * *